United States Patent [19]

Melsky et al.

[11] Patent Number: 5,147,483
[45] Date of Patent: Sep. 15, 1992

[54] IMPLANTABLE INFUSION DEVICE AND METHOD OF MANUFACTURE THEREOF

[75] Inventors: Gerald S. Melsky, Lexington; Frank R. Prosl, Duxbury, both of Mass.

[73] Assignee: Therex Corporation, Walpole, Mass.

[21] Appl. No.: 509,564

[22] Filed: Apr. 13, 1990

Related U.S. Application Data

[62] Division of Ser. No. 343,914, Apr. 26, 1989.

[51] Int. Cl.$^5$ .................. B23K 11/02; B29C 61/02
[52] U.S. Cl. .................................. 156/86; 219/105; 219/107; 264/230; 264/249
[58] Field of Search .................. 156/86; 264/249, 230; 604/93, 167, 175, 281, 891.1; 219/104, 105, 107, 118

[56] References Cited

U.S. PATENT DOCUMENTS

| | | | |
|---|---|---|---|
| 3,402,710 | 9/1968 | Paleschuck | 604/175 |
| 3,638,649 | 2/1972 | Ersek | 604/175 |
| 4,151,392 | 4/1979 | De Luca | 219/118 |
| 4,273,983 | 6/1981 | Ogawa et al. | 219/118 |
| 4,412,573 | 11/1983 | Zdeb | 604/415 |
| 4,496,350 | 1/1985 | Cosentino | 604/175 |
| 4,673,394 | 6/1987 | Fenton et al. | 604/175 |
| 4,772,270 | 9/1988 | Wiita et al. | 604/175 |
| 4,904,241 | 2/1990 | Bark | 604/175 |
| 4,905,682 | 3/1990 | Khayat | 604/175 |
| 4,929,236 | 5/1990 | Sampson | 604/175 |
| 5,006,115 | 4/1991 | McDonald | 604/175 |

FOREIGN PATENT DOCUMENTS

| | | | |
|---|---|---|---|
| 0119596 | 9/1984 | European Pat. Off. | 604/175 |
| 0309092 | 3/1989 | European Pat. Off. | 604/93 |
| 2612784 | 9/1988 | France | 604/891.1 |

Primary Examiner—Michael W. Ball
Assistant Examiner—Steven D. Maki
Attorney, Agent, or Firm—Cesari and McKenna

[57] ABSTRACT

An improved infusion device is of the type which can be implanted for drug delivery within a patient's body, and supplied with infusate without the need for surgical removal. The infusion device has a housing forming a chamber and an entry port into the chamber. The entry port is closed by a septum. The septum has a convex top section extending from the housing, and a frusto-conical section which matingly engages a similarly shaped interior surface of the housing. The interior surface can be provided with a plurality of notches with which the septum engages by material flexure. This arrangement improves retention of the septum and operation of the infusion device, and permits advances in the method by which such devices are manufactured.

6 Claims, 1 Drawing Sheet

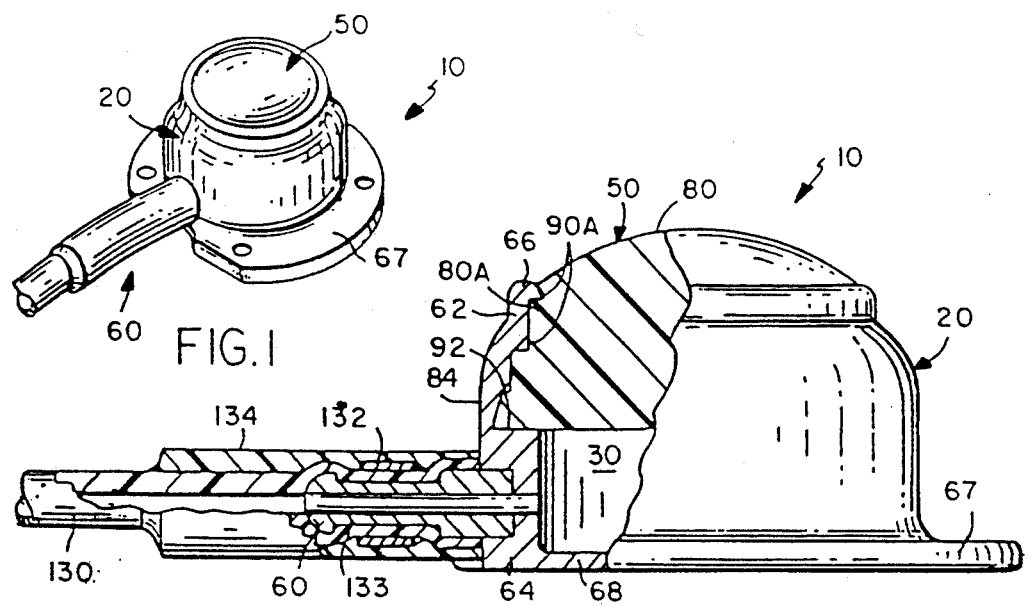
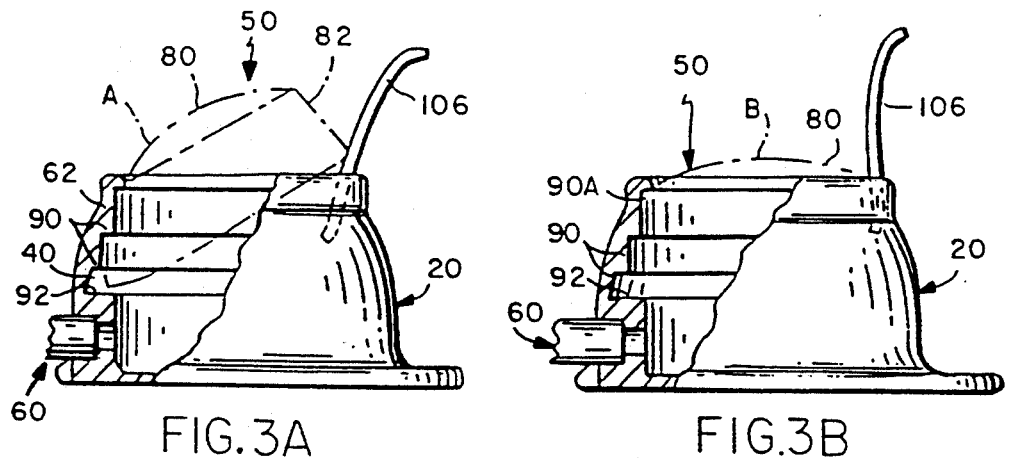
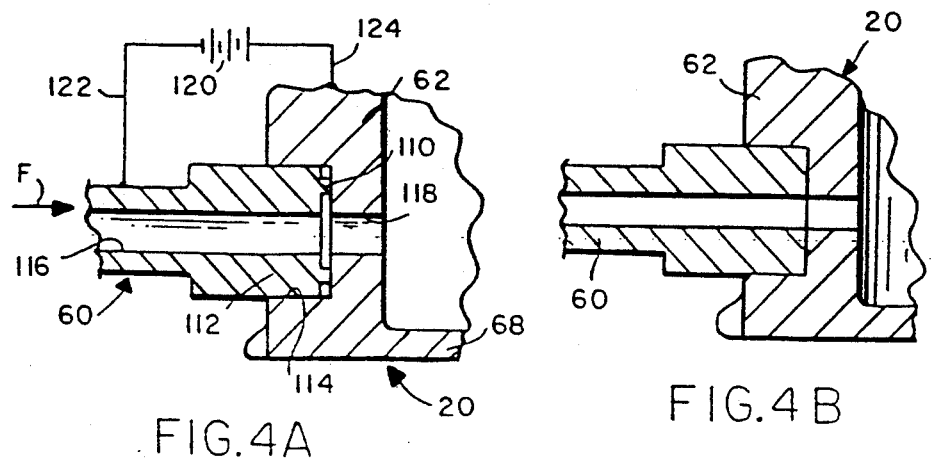

IMPLANTABLE INFUSION DEVICE AND METHOD OF MANUFACTURE THEREOF

RELATED APPLICATION

This application is a division of Ser. No. 343,914, filed Apr. 26, 1989.

FIELD OF THE INVENTION

This invention relates to an improved infusion device of the type which can be implanted for drug delivery within a patient's body, and supplied with infusate without the need for surgical removal.

BACKGROUND OF THE INVENTION

Relatively recently, infusion ports or portals have been developed which can be implanted in the body and remain there for a prolonged period of time by being serviced percutaneously without having to be removed from the body. Infusate is injected into the port by means of a conventional hypodermic syringe.

Known infusion devices of this general type have an infusate chamber formed within a housing of cup-like configuration with a top end closed by a needle-penetrable, resealable septum. The septum is typically a flat block of rubber contained, for example, axially within a cylindrical channel formed near the open end of the housing. With this arrangement, the exposed surface of the septum is generally recessed within the housing. The chamber is situated immediately below the septum for receiving the infusate. The infusate is delivered to a desired site within the patient by means of a catheter connected to a hollow stem leading from the chamber.

Typically, such infusion devices are made by first joining the stem to an open-ended, cylindrical wall of the housing. This is often accomplished by electron beam welding the stem along the inside of the cylindrical wall. In this operation, the welding head typically directs the electron beam through the open bottom end of the housing wall against the inner end of the stem to form a continuous weld bead. Then, the weld area is cleaned and polished to remove all traces of weld debris. When this is done, the septum is inserted into the housing from below, and positioned so as to close the top end. A top wall of the housing channel extends partially over the top of the septum and a ledge in the channel engages under the septum to prevent the septum from being dislodged vertically. Subsequently, the bottom end of the housing is closed by a base plate which is welded into place all around the housing. The base's external weld seam area is then cleaned.

This method of construction, and particularly the welding and finishing operations, tends to be exacting, tedious and expensive. Needless to state, the welds must be fluid impervious to prevent leakage of infusate from the housing. Furthermore, the quality of the finish of the weld seam about the base plate must be assuredly high to avoid sites conducive to bacterial growth after implantation. A complication in welding and finishing the base plate's weld seam is the presence of the septum. Extreme care must be taken not to damage or contaminate the septum during these procedures, making automated manufacture of such devices quite difficult, if not impossible.

While such prior art infusion ports are generally suitable for their intended purpose, although not entirely satisfactory, certain inherent limitations and inadequacies have been identified.

It is apparent from the foregoing description that if the infusion device is to have a long service life after it is implanted in the body, the penetrable septum must be capable of retaining its sealing properties even after a large number of injections. In other words, the hypodermic needle used to inject the infusate into the device must not "core" the septum so as to create possible avenues of leakage therethrough.

Also, when injecting infusate into the portal it is important that the hypodermic needle completely penetrate the portal's septum with only one puncture of the patient's epidermis to avoid undue discomfort to the patient and to assure that the infusate being injected flows into the device's chamber as it is supposed to, rather than being deposited locally in the patient's body and causing possible harm to the patient. Bearing in mind that such implantable devices actually move to some extent in the patient's body and may be situated at different depths below the skin depending upon the weight of the patient, proper targeting of the hypodermic needle on the infusion device's penetrable septum is not a simple matter. This is all the more the case considering that it is desirable to make implantable devices of this type as small and compact as possible so as to occupy a minimum amount of space in the body. Not only that, but the arrangement by which the septum is retained typically restricts the exposed surface of the septum to a mere fraction of its total area, making it an even smaller target.

Another disadvantage arises out of the configuration of the top end of the housing in which the septum is seated. By virtue of the fact that the septum is recessed in the housing, a generally flat surface is presented to the skin of the patient. This creates the opportunity for seroma or pocket formation at the top of the device. Such a dead space may collect body fluid thereby promoting bacterial growth and infection or collect fibrin that can interfere with access to the chamber. Such an irregular, unyielding surface at that end of the portal also raises the potential for abrasion and tissue breakdown if palpation is used to locate the infusion port in order to service it.

SUMMARY OF THE INVENTION

Accordingly, the present invention aims to provide an implantable, percutaneously accessible infusion device of improved construction.

Another object of the invention is to provide an implantable infusion device made by an improved method of high precision manufacture which is less exacting, tedious, and expensive than for known devices, while at the same time produces a device of high quality.

Still another object of the invention is to provide an infusion port or portal having improved septum and housing configurations, with almost no dead space at which body fluid or fibrin can collect and promote infection or interfere with access to the port.

A further object of the invention is to provide an infusion port having an atraumatic profile which, on subcutaneous implantation, presents a rounded and smoothly contoured, cushioned surface to the overlying tissue to create a congruent interface therewith.

It is a more general object of the present invention to provide an improved implantable infusion device which overcomes to some extent the above-mentioned limitations and disadvantages of the prior art.

Other objects of the invention will, in part, be obvious and will, in part, appear hereinafter.

The invention accordingly comprises the features of construction, combination of elements and arrangement of parts which will be exemplified in the following detailed description, and the scope of the invention will be indicated in the appended claims.

Briefly, an implantable, infusion port or portal in accordance with the invention has a housing forming an infusate chamber and an entry port into the chamber, a self-sealing, penetrable septum of resilient material disposed on a ledge or shoulder portion of the housing for closing the entry port, and a fluid outlet passage from the chamber for delivering infusate therefrom to a selected infusion site in the body.

In accordance with a first aspect of the invention, the septum is generally dome-shaped, with a convex top extending from the housing, and an insignificant top margin or lip of the housing being present around the edge of the septum. This improved geometry for the septum is intended to provide superior service during repeated use of the device. The dome-shaped septum combines increased depth and improved shape to more securely engage a hypodermic needle, even during lengthy ambulatory infusion. The larger exposed surface area and increased number of possible puncture paths through the septum extends its useful life by preserving the self-sealing properties of the septum over a greater number of infusions. Furthermore, the infusion device presents a rounded, cushioned surface to overlying tissue, to create a congruent interface without dead space between skin and device.

In accordance with a second aspect of the invention, the septum is retained by an improved arrangement. In an exemplary practice of the invention, the septum is provided with a frusto-conical side surface widening away from the convex top. An interior surface of the housing adjacent to the entry port is contoured so as to narrow towards the free end of the housing, mating with the frusto-conical wall of the septum and, thereby, holding the septum in place. In a preferred practice, the interior surface is formed with a plurality of axially-spaced notches or step-like overhangs extending, for example, circumferentially about the entry port. The septum resiliently grips the notches, which therefore exert axially- and radially-acting holding forces on the septum. Further, the top-most notch is located at or near the free end of the housing so as to extend radially a short distance over the convex top of the septum for additional vertical containment of the septum.

The forces generated by this septum-retaining arrangement not only hold the septum, but also improve needle engagement and retention. While the conventional septum described above employs axial "squeeze" across a thin horizontal plane to hold the needle, this improved septum retaining arrangement exerts radially acting, compressive forces substantially throughout the septum's thickness for improved needle-holding force distribution. Also, it improves the self-sealing characteristics of the septum.

The invention embraces not only the improved infusion device described briefly hereinabove and in greater detail below, but also an improved method of making such devices.

The method entails the steps of providing a housing preferably of one-piece integral construction, welding a hollow stem to the exterior of a wall section of the housing for forming an outlet passageway, cleaning and otherwise finishing the continuous weld seams produced by the foregoing welding step, and, only after the welding and finishing steps, seating the septum in the entry port by installing the septum from the top end of the housing. Since the septum is inserted after the welding and finishing steps are completed, there is no danger that such steps may damage the septum.

Where the septum retaining arrangement includes the notched and contoured interior housing surface, the septum is installed by shoehorning the septum into place in the housing, which entails resiliently compressing the septum laterally with an installation tool while driving the septum downward into its seat at the housing interior surface. When seated, the septum resiliently engages and interfits with the housing interior surface due to the elastic restoring forces generated within the septum material itself. In this way, the septum is preloaded with radial force components so that it is very securely retained in its seat, able to more securely engage a syringe needle that penetrates it, and better able to reseal itself after needle puncture.

The stem welding step in one practice of the invention entails providing the stem with an axially-extending circular ridge of reduced cross-section at one end thereof. This end is then seated within a socket formed with a housing wall. Resistance welding is employed to generate sufficient heat so as to melt the ridge and flow the melted material about the stem end, thus creating a secure butt weld with the wall of the socket.

The foregoing manufacturing techniques provide improved structural strength and integrity and reduce the potential for leakage. Overall, they provide an improved method of high precision manufacture of a quality infusion device easily adaptable to automation. Furthermore, by employing single-piece construction for the housing, dead spaces and cracks are eliminated which otherwise could trap blood, drugs or bacteria. This construction of the port also enables it to be more easily flushed clean.

BRIEF DESCRIPTION OF THE DRAWING

For a fuller understanding of the features, advantages, and objects of the invention, reference should be made to the following detailed description and the accompanying drawing, in which:

FIG. 1 is a perspective view of an infusion port in accordance with the invention;

FIG. 2 is an enlarged side view, partially cut away, of the infusion port of FIG. 1 showing aspects of its internal construction;

FIGS. 3A and 3B are partial side views, partially cut away, of the infusion port of FIG. 1 along with a septum-installation tool being used at different times during assembly; and FIGS. 4A and 4B, respectively, are enlarged detail views in section of the housing-to-stem joint before and after welding.

DETAILED DESCRIPTION OF AN ILLUSTRATIVE EMBODIMENT

Referring now to FIGS. 1 and 2, there is shown an implantable, infusate portal 10 made in accordance with an illustrative practice of the invention. In use, such devices are typically subcutaneously implanted for delivery of an infusate, although in some instances they are used for removal of a body fluid, e.g., blood. For example, such devices can provide for controlled drug delivery to a selected infusion site in a human or animal body for any of a variety of therapeutic purposes.

The illustrated infusion portal 10 has a cup-like housing 20 forming an infusate chamber 30 and an entry port 40 (see FIG. 3A) into the chamber 30, a self-sealing, penetrable septum 50 of resilient material for closing the entry port 40, a fluid outlet passage in the form of a tubular stem 60 from the chamber 30 for selectively delivering infusate therefrom. The infusion portal 10 is accessed by means of a conventional hypodermic syringe (not shown)—i.e., the syringe needle penetrates the septum 50 and injects a fresh charge of infusate into the chamber 30. On removal of the needle, the septum 50 seals itself. This process is repeatable as needed over the implanted life of the device.

The housing 20 is preferably of unitary construction, hermetically sealing its infusate contents. Desirably also, the housing is made of a rigid material, for example, titanium, while the septum 50 is made of an elastic material such as silicone rubber. These materials are selected for their inertness, endurance, lightness, and biocompatibility and the housing 20 and stem 60 being capable of being fusion welded.

More specifically, the illustrated housing 20 is formed by a generally tubular side wall section 62 disposed about the chamber 30 and entry port 40 and having lower and upper ends, designated 64 and 66 respectively. The lower end 64 is provided with a radially-extending flange portion 67 for mounting the device. The housing 20 also has a bottom or base 68 for closing the lower end of the wall section 62. The septum-filled entry port 40 is located proximate to the upper end 66. This end constitutes the free edge or top margin of the wall section 62. The entry port 40 extends axially therefrom approximately half of the distance to the base 68. As depicted, the chamber 30 makes up the balance of the space within the housing 20. Further details of the housing 20 shall be given below, but first it is necessary to describe the novel geometry of the septum 50.

As can be seen in FIGS. 2 and 3A, the illustrated septum 50 is generally shaped as a dome, having a rounded convex top section 80 and a generally frusto-conical (at least in its undeformed state) bottom section 82. After installation, as depicted in FIG. 2, the septum 50 is seated in the entry port 40 with its convex top section 80 extending from the housing 20 beyond the top edge margin 66 thereof. An exterior portion 84 of the illustrated housing wall section 62 is laterally rounded so as to complete the generally hemispherical geometry of the device, and provide the infusion port 10 with a smoothly contoured, aesthetically-pleasing appearance.

The septum's geometry provides a large usable surface area on the septum in the order of 0.2 square inches (or approximately 0.5 inches across) making it an easy target for the hypodermic needle used to access the device after implantation. In other words, nearly the entire top surface of the infusion device consists of septum, the housing edge margin 66 around the septum being as small as practical, e.g, 0.06 inches (0.15 cm). Furthermore, the convex top section 80 of the septum 50 eliminates the dead volume that exists at the surface of block-like septums of implanted prior art devices of this type. As mentioned above, body fluids can collect there and promote bacterial growth. For this reason, the housing 20 has been provided with a smooth curvilinear exterior to the maximum extent possible. On implantation of the improved infusate port 10, the dome-shaped septum 50 presents a cushioned, congruent interface to the overlying tissue, echoing the natural body contours.

Overall, the geometry of the infusate port 10 has been designed to better fulfill the port's medical purposes as an implanted infusate delivery device. Similarly, the arrangement by which the septum 50 is retained within the housing 20 has been designed to improve the performance of the infusion port 10.

As illustrated, the interior surface of the wall section 62 that defines the entry port 40 is specifically contoured so as to retentively engage and grip the frusto-conical section 82 of the septum 50. This is achieved in the depicted embodiment by giving that interior surface a matching generally frusto-conical configuration with superimposed axially-spaced, substantially-rigid notches or steps 90 that extend all around the entry port 40, and a relatively wide annular ledge or shoulder 92 at the bottom of port 40. The notches 90 form a series of axially-spaced-apart circumferential overhangs that extend above ledge 92. The outer diameters of the overhangs 90 are all larger than the inner diameter of ledge 92 even as they become progressively smaller towards the top of port 40. In other words, the illustrated frusto-conical interior surface narrows nearer the top edge margin 66 of the housing 22. The septum 50, which is inserted into port 40 in a manner to be presently described, seats on ledge 92. In this position, the septum 50 compressively engages the wall of port 40 so that the overhangs 90 deform the side of septum section 82 to create a series of notches or steps 94 there which interlock with those overhangs to prevent upward displacement of the septum from its seat on ledge 92.

To assure a very positive retention of the septum 50 in port 40, the upper-most notches 90A are designed so as to extend over a portion of the convex top section 80 of the septum 50. This portion is insubstantial in radial extent though sufficient to vertically contain the septum 50. Those interfitting notches 80A and 90A prevent blowouts due to internal pressure. Thus, while known prior art infusion devices can handle internal pressures of 125 psi, the improved retention arrangement just described can safely accommodate pressures of 200 psi or more.

Assembly of the septum 50 into the housing 20 shall now be described with reference to FIGS. 3A and 3B. The use of a domed, frusto-conical septum shape in combination with the retaining arrangement described above enables the septum 50 to be inserted into the entry port 40 from the top of the housing 20. To do this, the septum 50 is cocked and inserted into the entry port 40 so that its lower edge rests on ledge 92 as shown in FIG. 3A. Then an installation tool 106 similar to a shoe horn is inserted into the top of port 40 at the opposite side of the septum. A downward force applied to the side of the septum along with a lateral jacking force applied via tool 106 wedge the septum into the port so that its bottom edge margin seats on ledge 92 as shown in FIG. 3B. Due to the elastic restoring forces generated within the material of the septum 50, the septum section 82 deforms about and conforms to the notches 90. In effect, the notches 90 dig into the septum 50, gripping it and holding it in place. With the septum 50 properly seated and retained, its top section 80 extends in dome-like fashion above the housing 20.

With the septum 50 inserted from the top of the housing 20, it is not necessary nor desirable to use the conventional approach to manufacturing the housing 20.

As such, a further aspect of the invention relates to the improved fabrication of a hermetically sealed housing structure for the infusion port 10. With reference to FIGS. 1 through 3B, the improved fabrication process starts for purposes hereof with the stem 60 being fusion welded onto the exterior wall of section 62 with a continuous weld seam. The weld seam then is cleaned and otherwise finished. Not until the welding and finishing steps are completed is the septum 50 inserted, as described above.

A novel method of securing the stem 60 to the housing 20 shall now be described with reference to FIGS. 4A and 4B. The stem 60 is furnished (as by machining) with a circular ridge 110 of reduced cross-section at one end of 112 thereof. The stem 60 and housing 20 are then assembled as depicted by seating the stem end 112 in a socket 114 formed in the wall section 62. As can be appreciated from the drawing, the desire here is to align an axial passage or bore 116 in the stem 60 with a through-hole 118 in the housing 20. As such, the through-hole can be formed as a stepped or countersunk bore with the socket 114 being the wider, larger diameter portion thereof. Resistance welding is then employed to generate sufficient heat to melt the ridge 110, and flow the melted material about the stem end 112, creating a secure butt weld with the wall of the socket. This is achieved by applying an axially directed force, as indicated by arrow "F" in FIG. 4A, while establishing a DC voltage potential between the electrically-conductive wall section 62 and stem 60. This is represented schematically by the battery 120 and leads 122, 124 for electrically connecting the battery 120 to the stem 60 and wall section 62, respectively, so as to complete the circuit. In practice, the applied force can be approximately twenty to thirty pounds, while approximately 75 watt seconds of welding energy achieved by capacitive discharge is applied. The resulting welded, hermetically-sealed joint is shown in FIG. 4B.

It is noteworthy that the foregoing method of securing the stem 60 permits it to be welded from the outside of the housing 20. In the prior art described above, the welding was done from within the housing, necessitating an awkward angle of attach for the welding tool. Another reason to avoid inside welds is that it discolors the area around the weld seam and creates debris within the housing which has to be cleaned out, typically a difficult, time consuming process. Also, conventional welding techniques typically require that the device be placed in an inert gas atmosphere. The present invention's improved approach can be efficiently performed in the open, using otherwise conventional welding apparatus and procedures that are readily automated. In fact, the entire manufacturing process described herein can be automated for economic fabrication of the infusion port 10.

With the housing 20, stem 60 and septum 50 formed, it is only necessary to attach a flexible catheter to complete the device. Here, too, an improved arrangement is proposed, as shown in FIG. 2. As illustrated there, an end of the catheter 130, which should be made of a biocompatible material, e.g., silicone rubber, is slid onto the stem 60 and retained there by using a crimp ring 132 to press the catheter radially into sleeve a narrowed stem portion 133. If desired, sleeve 134 can also be used to hold the catheter in place. The sleeve 134 preferably is made of a plastic material which can be shrink fitted over the catheter. In one example, a silicone rubber sleeve is used which expands when immersed in Freon prior to being installed and when dry shrinks radially around the catheter. Also, silicon adhesive can be applied to the inside surface of the sleeve 134 and at its end surface abutting the housing 20 to assure a fluid tight seal between the sleeve 134 and both the catheter 130 and the housing 20.

The foregoing description has been limited to a specific embodiment of this invention. It will be apparent, however, that variations and modifications may be made without departing from the spirit of the invention. For example, the convex top of the septum can be formed from a series of short planar segments rather than being a single smooth frusto-spherical segment. Furthermore, other forms of ridges or projections can be substituted for the retaining notches.

It is accordingly intended that all matter contained in the above description or shown in the accompanying drawing be interpreted as illustrative rather than restrictive, with the scope of the invention being indicated by the appended claims. All changes which come within the meaning and range of equivalency of the claims are therefore intended to be embraced therein.

Having described this invention, what is claimed as new and secured by Letters Patent is:

1. A method of manufacturing an implantable infusion apparatus having:
   (a) housing means for forming an infusate chamber, said housing means including:
      (i) a generally tubular wall section disposed about said chamber, said wall section including an interior surface,
      (ii) a base closing said wall section proximate a bottom end thereof,
      (iii) an entry port into said chamber at a top end of said housing means, and
      (iv) a ledge disposed intermediate said entry port and chamber,
   (B) means for closing said entry port including a self-sealing, penetrable septum of resilient material disposable on said ledge,
   (C) means defining a fluid outlet passage from said chamber for selectively delivering infusate therefrom, said passage defining means including a hollow exterior stem having a stem end and connected to said housing means,
   said method comprising the steps of:
      forming a socket in said wall section,
      providing said stem end with a circular ridge of reduced cross-section,
      seating said stem end in said socket;
      generating sufficient heat by resistance welding so as to melt said ridge and flow the melted material about said stem end thereby creating a secure butt weld with said wall section,
      after said joining step, disposing said septum on said ledge to close said entry port, including installing said septum from said top end of said housing, and
      retaining said septum at least partially within said entry port.

2. The method of claim 1 wherein said septum-installing step includes compressing said septum laterally, and driving said septum into said entry port.

3. The method of claim 2 and further including forming said interior surface with a plurality of overhanging notches with which said septum resiliently mates by material flexure thereof.

4. The method of claim 1 and further including forming said septum with a convex top, and said installing step includes disposing said septum partially within said entry port and partially extending therefrom so as to expose said convex top.

5. The method of claim 1 and further including sliding a catheter segment over said stem after said stem joining step, and retaining said catheter segment to said stem by a crimping ring.

6. The method of claim 5 wherein said catheter retaining step further includes sliding a shrinkable sleeve over said ring and said segment, and shrinking said sleeve.

* * * * *